United States Patent [19]
Paulson

[11] 3,989,383
[45] Nov. 2, 1976

[54] REACTION DETECTION SYSTEM
[75] Inventor: Gerald Lee Paulson, Hollywood, Fla.
[73] Assignee: Bio-Technology Instruments Corporation, Hialeah, Fla.
[22] Filed: Apr. 7, 1975
[21] Appl. No.: 565,665

[52] U.S. Cl............................... 356/96; 23/230 B; 356/201
[51] Int. Cl.²...................... G01J 3/42; G01N 21/00
[58] Field of Search...................... 356/96, 97, 201; 23/230 R, 230 B; 195/103.5 R

[56] References Cited
UNITED STATES PATENTS

| | | | |
|---|---|---|---|
| 3,701,601 | 10/1972 | Plumpe, Jr. et al.................. | 356/96 |
| 3,810,696 | 5/1974 | Hutchins, Jr...................... | 356/97 X |
| 3,881,992 | 5/1975 | Ralston............................ | 356/96 X |

*Primary Examiner*—John K. Corbin
*Assistant Examiner*—Rolf Hille
*Attorney, Agent, or Firm*—Silverman & Cass, Ltd.

[57] ABSTRACT
A system for detecting the reaction rate of change of a solution. Enzyme activity of a sample may be measured by such a system. In the system, the light transmittance characteristic of the sample changes in accordance with the reaction change. Detection circuitry detects the variation in light absorbance and develops an electrical signal which varies in accordance with the absorbance, thus varying in accordance with the reaction change. First sampling circuitry samples the electrical signal at predetermined first intervals and develops a first sampling signal during that sampling which is proportional to the electrical signal. This first sampling signal is held in the first sampling circuitry until the following sampling. Second sampling circuitry samples the first sampling signal at predetermined intervals and develops a second sampling signal during the sampling which is proportional to the first sampling signal. The second sampling signal is held in the second sampling circuitry until the following sampling. The first and second sampling signals are summed to develop an output signal which represents the difference between the first and second signals and is therefore an indication of the reaction rate of change between sampling intervals. A scaling factor is added to this output signal for converting the signal into known and recognized units such as optical absorbance and the converted signal is displayed on a display device.

24 Claims, 3 Drawing Figures

REACTION DETECTION SYSTEM

BACKGROUND OF THE INVENTION

The present invention relates to reaction rate detection systems and more particularly to such systems employed for photometric analysis of reaction rate of enzyme activity.

With certain types of solutions, it is important to determine the rate of change or reaction rate of the solution in the presence of certain catalysts. For example, placing an enzyme in certain types of solutions will cause a chemical reaction to occur. The enzyme acts as a catalyst and causes the reaction, but it does not enter into the reaction. However, the rate of change or reaction rate of the solution does indicate enzyme activity and enzyme activity is a measure of the enzyme concentration.

With certain types of enzyme reaction rate photometric analysis, the light absorbance of an enzyme reaction within a cell is continuously monitored at a predetermined light frequency and the electrical output of a photomultiplier or other photodetector is recorded. A technician then can perform a differentiation in order to determine the reaction rate or it may be performed by a computer. Circuitry which can provide a continuous differentiation function in response to an electrical signal can be provided. However, it is complex and expensive.

In the foregoing type of analysis, it is possible for the electrical photodetector signal to exhibit variations and discontinuities. For example, such results can occur when a measurement is taken before the reaction has stabilized at a constant rate. Furthermore, depending upon the type of reaction, the reaction rate may follow a linear pattern initially and then diverge from the linear pattern. Signals exhibiting these variations must be identified so that they may be discarded and/or the test terminated and a new test initiated. As with the reaction rate determination this type of analysis has been performed by a technician or a computer. Circuits which have been heretofore available for performing these functions have performed them on a continuous basis. Most commonly a differentiating circuit identical to the previously noted differentiating circuit is employed. As noted above, such circuits are complex and expensive.

Generally in systems performing the above-noted analysis a calibration is provided. The calibration allows the system to provide an output directly readable in terms of known units of measurements such as absorbance units (ABS) or international units (I/U). When such calibrations are provided, the analysis requires particular volumes of solution and enzyme, and generally a particular reaction temperature. It is not possible to use different volumes or different temperatures without entirely recalibrating the system.

SUMMARY OF THE INVENTION

In practicing this invention, a system is provided for detecting the reaction rate of change of a solution whose optical opacity changes in accordance with the reaction change therein. This system includes a detection circuit for developing an electrical signal which varies in accordance with the optical opacity thus varying in accordance with the reaction change. First sampling circuitry is operable at predetermined intervals to sample the electrical signal developed by the detection circuit and develop a first sampling signal during this sampling. The first sampling signal is proportional to the electrical signal sampled and is held in the first sampling circuit until the following sampling is taken. A second sampling circuit samples the first sampling signal stored in the first sampling circuit at predetermined second intervals and develops a second sampling signal during the sampling. This second sampling signal is proportional to the sampled first sampling signal and is held in the second sampling circuit until the succeeding second sampling signal. A summing circuit connected to the first and second sampling circuits receives the first and second sampling signals stored therein and develops an output signal which represents the difference between the first and second sampling signals. As the period between the existing first and second sampling signal is known, the difference between the first and second sampling signals, which is the output signal, represents a particular rate of change for a known interval. This output signal is coupled to a display device where it is displayed for indicating the reaction rate of change.

DETAILED DESCRIPTION OF THE PREFERRED EMBODIMENT

Figure 1:
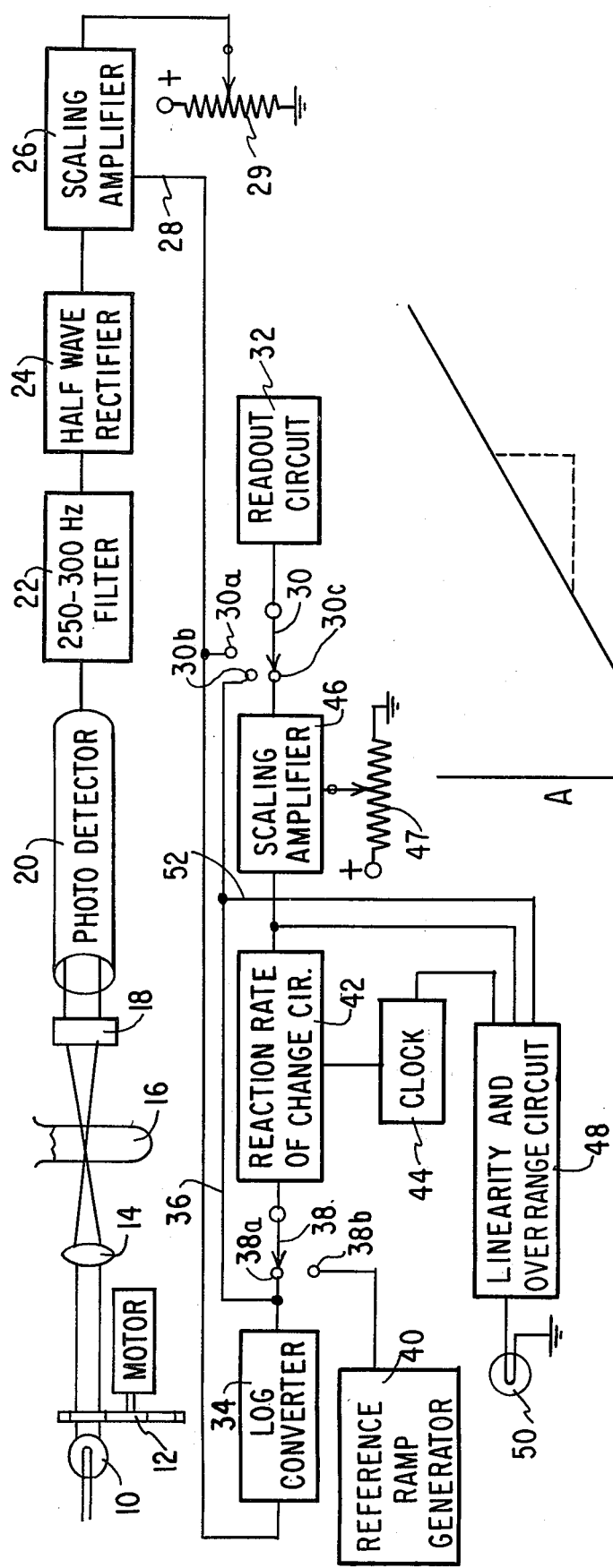
FIG. 1 is a block diagram of the reaction detection system of this invention.

Referring to FIG. 1, a lamp 10 produces light which is passed through a chopper 12. Chopper 12 consists of a motor driven disc having a number of holes positioned around the circumference of the disc which pass through the disc. Chopper 12 acts to chop the light beam directed from lamp 10 to lens 14. In the preferred embodiment, the light beam is chopped at approximately a 300 cycle per second rate producing light pulses having approximately a 300 cycle repetition rate. These light pulses are directed by lens 14 to cuvette 16.

Cuvette 16 includes at least two walls which are formed from a light transmitting material such as glass or plastic. In the embodiment shown it is formed entirely from glass or plastic and contains the solution to be analyzed. For example, the solution can be a reagent containing NADH plus buffer. Human sera containing the enzyme is added to the solution. The light directed from lens 14 passes through curvette 16 and the solution and enzyme contained therein to filter 18.

Filter 18 is designed such that it blocks all but particular wavelengths of light. In the preferred embodiment, filter 18 includes four different sections, any one of which may be moved into the light beams path. Each section allows passage of different discrete wavelengths of light. One of the four sections will allow passage of only the 340 nanometer wavelength. For purposes of this application, we will consider only the passage of this one wavelength. The light which passes through filter 18 is coupled to a photodetector 20 which develops a voltage that is proportional to the intensity of the light coupled to photodetector 20.

As noted previously, the light signals from lamp 10 are chopped by chopper 12. Accordingly, the light signals received by photodetector 20 are interrupted at predetermined intervals and have a predetermined repetition rate. The voltage developed by photodetector 20 also will have a predetermined repetition rate which corresponds to the repetition rate of chopper 12. In the preferred embodiment, photodetector 20 will develop voltage signals of predetermined duration at a 300 cycle per second repetition rate.

The voltage signals developed by photodetector 20 are coupled to filter 22. Filter 22 passes only signals in the 250 to 300 cycle range so that the signals developed in response to the light pulses transmitted from lamp 10 and chopper 12 will be passed through filter 22. All extraneous signals such as those developed from ambient light produced, for example, by fluorescent fixtures, will be blocked by filter 22. The pulses passed through filter 22 in addition to varying in accordance with the repetition rate of the light, will also vary in amplitude in accordance with the intensity of the light. The signals passed through filter 22 are coupled to a half wave rectifier 24 where they are rectified and filtered to produce a d.c. signal which varies in accordance with the variations in amplitude of the voltage signals received. The d.c. signal developed by rectifier 24 is coupled to a scaling amplifier 26.

When a chemical and reagent in a cuvette are initially placed in the light beam, before a reaction begins, the optical transmittance of the chemical could be high resulting in a relatively high voltage being developed at the output of rectifier 24. It is also possible for the optical transmittance to initially be relatively low so that a relatively low voltage will be developed at the output of rectifier 24. Scaling amplifier 26 amplifies the voltage developed by rectifier 24 and includes a potentiometer 27. Potentiometer 27 allows the voltage developed at the output of amplifier 26 to be adjusted to a predetermined reference voltage. In the preferred embodiment, a cuvette containing water is placed into the system and potentiometer 27 is set such that the voltage at conductor 28, the output of amplifier 26, is 10 volts. A 10 volt signal is within the operating range of the remaining circuitry, and allows the voltage which is produced at the end of the reaction cycle, when 10 volts is initially selected, to be well within the operating range of the circuitry. The adjustment of potentiometer 27 is simplified via a connection between conductor 28 and a readout circuit 32 provided by a switch 30.

Switch 30 is a single pole three position switch in the preferred embodiment. When the arm of switch 30 is moved to terminal 30a, the connection between conductor 28 and readout circuit 32 is provided. Readout circuit 32 can be any one of a number of well known devices which produce a visual or written record of the received voltage signal. In the preferred embodiment, readout circuit 32 is a digital voltmeter which provides a direct visual display of the voltage. When switch 30 is connected as described and a cuvette 16 is initially placed in position, potentiometer 27 can be adjusted so that the voltage reading shown on the readout circuit 32 is ten volts.

The output of scaling amplifier 26 also is coupled via conductor 28 to a log converter circuit 34. The voltage on conductor 28 varies in accordance with the optical transmittance of the chemical in cuvette 16. Optical absorbance is defined as the logarithm of the reciprical of optical transmittance. For chemical reactions such as described herein, the optical absorbance as the reaction proceeds varies linearly with respect to time. Log converter circuit produces a voltage at its output which is the logrithmic equivalent of the reciprical of the voltage at its input. Accordingly, log converter 34 produces a signal at its output exhibiting all the characteristics of the optical absorbance of the chemical in the cuvette 16 including a linear change with respect to time as the reaction of the enzyme and chemical in cuvette 16 progresses. The output of log converter circuit 34 is coupled by conductor 36 and terminal 30b of switch 30 to readout circuit 32 so that readings may be taken of the optical absorbance of the sample initially and as the reaction progresses. The output of log converter 34 also is coupled to terminal 38a of switch 38.

A reference ramp generator 40 is coupled to terminal 38b of switch 38. When the arm of switch 38 is moved to contact terminal 38b, reference ramp generator 40 will begin to develop a ramp voltage at its output. The reference ramp generator 40 is a saturation amplifier having an output voltage which saturates at a predetermined level of, for example, 10 volts at the end of a twenty minute operating cycle. During the operating cycle of reference ramp generator 40, the voltage developed at its output will increase at a linear rate. The constants of the particular circuit employed for reference ramp generator 40 are selected such that the ramp voltage produced varies at a rate which is equivalent to an absorbance rate of change of one tenth absorbance unit per minute (0.1 ABS/1 min.). The purpose of reference ramp generator 40 will be more clearly explained at a subsequent point in this application.

The output voltage developed by log converter circuit 34 or the ramp voltage developed by reference ramp generator 40 is coupled via switch 38 to a reaction rate of change circuit 42. Reaction rate of change circuit 42 operates at predetermined time intervals to sample the voltage coupled thereto for a predetermined time period and develop a first sampling voltage which is related to the amplitude of the sampled voltage. Prior to each sampling the last developed sampling voltage is sampled for a predetermined time period to develop a second sampling voltage related to the amplitude of the first sampling voltage.

Circuitry within the rate of change circuit 42 compares the first sampling voltage received during a sampling with the second sampling voltage and develops a difference or comparison voltage which is related to the variations in amplitude of the compared sampling voltages. This comparison voltage, as it is based upon measurements which are separated by predetermined time intervals, is a measurement of the rate of change during that interval and is therfore a measurement of the reaction rate of change of the solution and enzyme in cuvette 16. Clock circuit 44 is coupled to reaction rate of change circuit 42 and develops the clock pulses which cause reaction rate of change circuit to sample the received voltage and to compare sequential samplings.

The comparison voltage developed by reaction rate of change circuit 42 is coupled to a second scaling amplifier 46. Scaling amplifier 46 amplifies the comparison voltage developed by reaction rate of change circuit 42 and includes a potentiometer 47 which allows the voltage developed at the output of amplifier 46 to be adjusted to any desired level.

In operation, switch 38 is connected to reference ramp generator 40 via contact 38b and switch 30 connects readout circuit 32 to the output of scaling amplifier 46 via contact 30c. With this connection arrangement, reaction rate of change circuit 42 will develop a comparison voltage at its output which is directly related to a rate of change of one tenth. ABS/min, because reference ramp generator 40 is designed to provide this rate of change. Potentiometer 47 then may be adjusted such that its output signal and accordingly the output displayed by the readout circuit 32 reads rate of change of absorbance da/dt or international unit (IU), or any other reference or standard measurement unit. The adjustment also may be made so as to take into consideration variations in the temperature of the solution in cuvette 16 and variations in the ratio of solution quantity to sample quantity. When the scaling amplifier 46 is so adjusted and switch 38 is connected to the output of log converter circuit 34 via contact terminal 38a, the reading at readout circuit 32 will be referenced to a rate of change of one tenth ABS/min. in whatever units of measurement are desired and will be a direct readout in the desired units.

Clock circuit 44 and the output of reaction rate of change circuit 42 also are coupled to a linearity and overrange circuit 48. Linearity and overrange circuit 48 performs two functions as indicated by its name. Circuit 48 stores the comparison voltage developed by circuit 42 and compares each comparison voltage with the succeeding comparison voltage developed at the output of circuit 42. If they are substantially identical, indicating that the reaction is proceeding in a linear fashion, linearity circuit 48 will produce no output. If, however, they are not identical and are different by a predetermined amount, linearity circuit 48 will develop an output signal which is coupled to a lamp 50 causing it to light. This indicates that the reaction is either proceeding in a nonlinear fashion, that the reaction has not stabilized or that some other condition has occurred in the reaction which would tend to invalidate any results obtained. However, the results obtained at that time by the reaction rate of change circuit and displayed in readout circuit 32 are shown notwithstanding the presence of an indication from lamp 50. This allows the technician to read the results of the test and, if the results are of value, to record them.

Linearity and overrange circuit 48 also is connected to the output of log converter 34 via conductor 52. If the output voltage of the log converter 34 exceeds 10 volts, which is equivalent to two absorbance units, thus exceeding the operating range of the system, overrange circuit 48 will produce an output signal which is coupled to lamp 50 causing it to light and indicate an out of range condition. In the preferred embodiment, overrange circuit 48 will operate causing lamp 50 to light when the voltage at the output of log converter 34 exceeds 10 volts.

Figure 2:
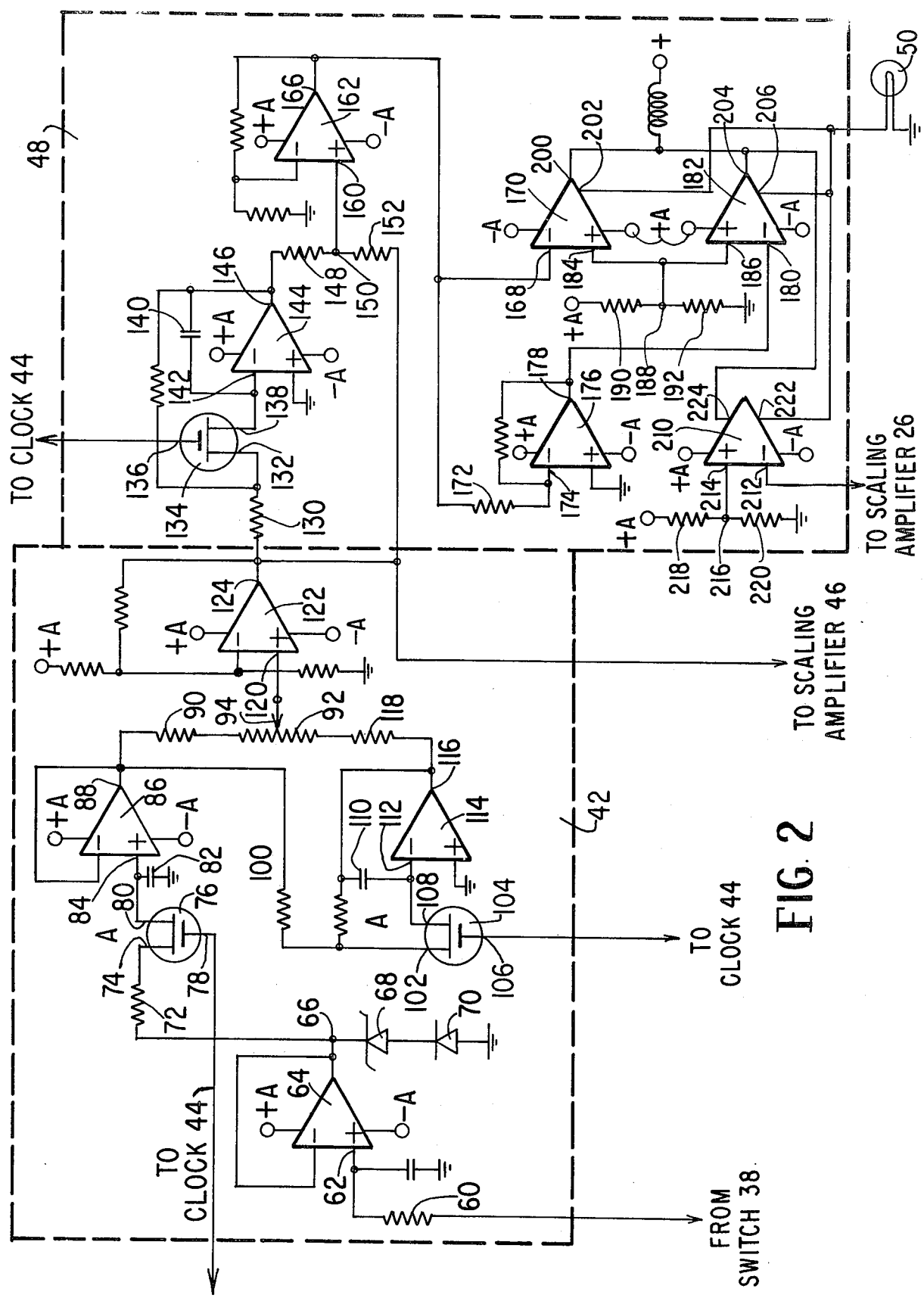
FIG. 2 is a schematic diagram of portions of the circuit shown in FIG. 1.

Referring now to FIG. 2, the reaction rate of change circuit 42 and the linearity and overrange circuit 48 are shown in greater detail. The voltage developed by log converter circuit 34 or reference ramp generator 40 is coupled from switch 38 through resistor 60 to input 62 of amplifier 64. Amplifier 64 amplifies the signals it receives and develops an amplified signal at output terminal 66. Zener diodes 68 and 70 connected to output terminal 66 are clamping diodes which prevent the output voltage of amplifier 64 from exceeding a predetermined positive value. The voltage developed by amplifier 64 is coupled from output terminal 66 through resistor 72 to the drain 74 of field effect transistor (F.E.T.) 76. Gate 78 of F.E.T. 76 is connected to clock 44 and source 80 of F.E.T. 76 is coupled to one terminal of capacitor 82 and to input 84 of amplifier 86. The second terminal of capacitor 82 is coupled to reference potential and the output of amplifier 86 is terminal 88.

Figure 3:
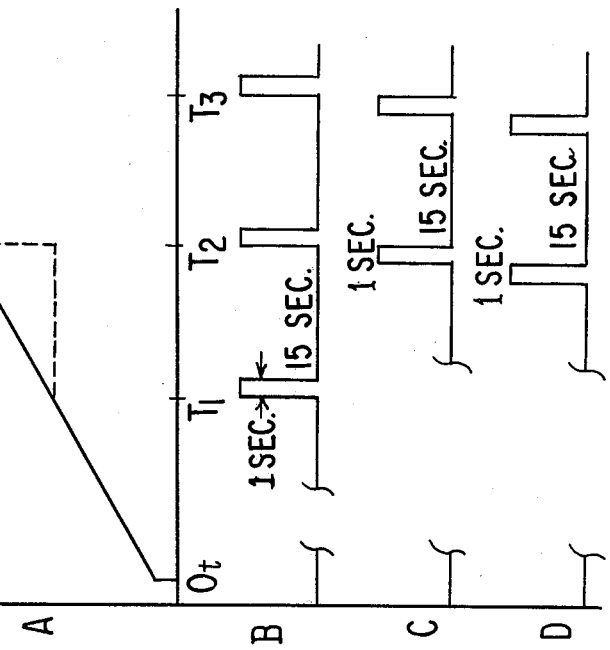
FIG. 3 includes waveform diagrams representing a linenar reaction and the clock pulses occurring at predetermined intervals during the indicated reaction period.

F.E.T. 76, capacitor 82 and amplifier 86 comprise a first sample and hold circuit. Referring to FIG. 3, waveform A is a graph of voltage versus time and it can, for example, represent a linear change of voltage exhibited at the output of log converter 34 when a reaction is proceeding in cuvette 16. Waveform B shows first clock pulses which are developed by clock circuit 44 and coupled to gate 78 of F.E.T. 76. As can be seen by reference to waveform B, the clock pulses each have a one second duration and are separated by a 15 second interval. The first clock pulse shown in waveform B occurs at time $T_1$, the succeeding first clock pulse occurs at $T_2$ and another clock pulse is shown as occurring at $T_3$. The clock pulse shown as occurring at $T_1$, when coupled to gate 78 of F.E.T. 76 will forward bias F.E.T. 76 allowing the signal at drain 74 to be coupled to capacitor 82. Capacitor 82 will begin to charge and will, within the one second interval for the first clock pulse, charge to a voltage which is proportional to the signal applied thereto and therefore proportional to the signal from log converter 34. Amplifier 86 is an operational amplifier having an extremely high input impedance and gain so that the voltage developed across capacitor 82 is also developed at output terminal 88. The voltage developed at output 88 is termed the first sampling voltage and is coupled through resistor 90 and potentiometer 92 to the wiper are 94 of potentiometer 92.

The first sampling voltage developed at output 88 of amplifier 86 is also coupled through a coupling resistor 100 to drain 102 of F.E.T. 104. Gate 106 of F.E.T. 014 is coupled to clock circuit 44 and receives second clock pulses shown in waveform C of FIG. 3. Source 108 of F.E.T. 104 is connected to one terminal of a capacitor 110 and to input 112 of amplifier 114. The output of amplifier 114 appears at terminal 116 and is coupled via resistor 118 and potentiometer 92 to the wiper arm 94 of potentiometer 92.

F.E.T. 104, capacitor 110 and amplifier 86 comprise a second sample and hold circuit. Following the operational cycle initialed above the clock pulse coupled to gate 106 of F.E.T. 104 is a second pulse shown in FIG. 3 waveform C as occurring just preceding the time $T_2$. This second clock pulse will forward bias F.E.T. 104 coupling the first sampling signal developed at output terminal 88 of amplifier 86 to capacitor 110. Capacitor 110 will begin charging in response to the voltage coupled thereto and will, within its one second interval charge to a voltage which is proportional to sampling voltage received. The voltage developed at output 116 of amplifier 114 is the same as the voltage developed across capacitor 110 and is termed the second sampling voltage.

For one small instant of time between the second clock pulse shown as occurring just prior to $T_2$ and the first clock pulse shown as occurring at $T_2$ in waveform B and C of FIG. 3, the outputs of amplifiers 86 and 114 will be the same. When the first clock pulse, shown in waveform B as occurring at the time $T_2$, is coupled to gate 78 of F.E.T. 76, the first sample and hold circuit consisting of F.E.T. 76, capacitor 82 and amplifier 86 will sample the voltage shown in waveform A as occurring at time $T_2$ and will develop a sampling voltage at output terminal 88 of amplifier 86 which is proportional to the voltage sampled. At the termination of the first clock pulse shown as beginning at time $T_2$ the first sampling voltage developed at output 88 of amplifier 86 will be proportional to the voltage shown as occurring at $T_2$ in FIG. 3 waveform A and the second sampling voltage developed at output 116 of amplifier 114 will be proportional to the voltage shown as occurring at time $T_1$ in FIG. 3 waveform A.

Resistors 90 and 118 and potentiometer 92 comprise a summing circuit. The first sampling voltage developed at output 88 of amplifier 86, after termination of the first clock pulse shown as being initiated at time $T_2$, is coupled through the resistor 90 to potentiometer 92. The second sampling voltage developed at output 116 of amplifier 114 at this same time is coupled through resistor 118 to potentiometer 92. The first and second sampling voltages coupled to potentiometer 92 are opposite in sign so that potentiometer 92 sums these two signals and develops a difference or comparison voltage which is equal to the difference between the two. This comparison voltage is developed at arm 94 of potentiometer 92 and is coupled to input terminal 120 at amplifier 122. Amplifier 122 acts simply to amplify the comparison voltage and couple the amplified voltage from output 124 to scaling amplifier 46 shown in FIG. 1 and to linearity and overrange circuit 48.

Output 124 of amplifier 122 is coupled through resistor 130 in linearity and overrange circuit 48 to drain 132 of F.E.T. 134. Gate 136 of F.E.T. 134 is coupled to clock circuit 44, and source 138 is coupled to one terminal of capacitor 140 and the input 142 of amplifier 144. The output of amplifier 144 appears at terminal 146 and is coupled through a resistor 148 to a junction 150. Junction 150 is also connected through a resistor 152 to the output 124 of amplifier 122.

F.E.T. 134, capacitor 140 and amplifier 144 constitute a third sample and hold circuit which is substantially the same as and operates in substantially the same manner as the first and second sample and hold circuits. Third clock pulses as shown in waveform D of FIG. 3 are developed by clock circuit 44. Each third clock pulse has a period of approximately 1 second and is separated from the succeeding and following clock pulse by 15 seconds. As can be seen by reference to FIG. 3, the third clock pulse terminates just before the beginning of a second clock pulse.

Again following the operational cycle initiated above, the third clock pulse occurring two seconds preceding the time indicated as $T_3$ in FIG. 3 is coupled to gate 136 of F.E.T. 134. This third clock pulse will forward bias F.E.T. 134 coupling the difference voltage developed at output 124 of amplifier 122 to capacitor 140. Capacitor 140 will begin to charge in response to the difference voltage and will within its one second interval charge to a voltage which is proportional to the comparison voltage sampled. Amplifier 144 is a high gain high impedance amplifier and is substantially the same as amplifiers 86 and 114. Consequently, the voltage developed at input 142 of amplifier 144 will also be developed at output terminal 146, the sign of the voltage developed at output terminal 146 will be inverted from the sign of the voltage developed at output terminal 124 of amplifier 122. The voltage developed at output terminal 146 of amplifier 144 is termed the third sampling voltage.

For one small instant of time, between the third clock pulse shown as occurring just prior to time $T_3$ and the second clock pulse occurring after termination of the previously noted third clock pulse, the voltage at output 124 of amplifier 122 and output 146 of amplifier 144 will be the same but opposite in sign. When the second clock pulse shown as occurring just preceding time $T_3$ terminates the comparison or rate of change voltage developed at the output of 124 of amplifier 122 will be the rate of change signal representing the rate of change of the voltage shown in waveform A between time period $T_2$ and $T_3$, and the third sampling signal developed at output 146 of amplifier 142 will be proportional to the rate of change signal representing the voltage shown in waveform A between time period $T_1$ and $T_2$.

Resistors 148 and 152 comprise a summing circuit. The voltage developed at output 124 of amplifier 122, representing the second comparison voltage in time is coupled from output 124 through resistor 152 to junction 150. The third sampling developed at output 146, representing the first comparison or rate of change voltage occurring in time is coupled through resistor 148 to junction 150. As previously noted, the two voltages are opposite in sign so that they will algebraically add at junction 150 and develop a voltage which is equal to the difference between the two. The voltage developed at the junction 150 is coupled to the input 160 of amplifier 162. Amplifier 162 amplifies the received signal and develops an amplified signal at output 166. The amplified signal developed at output 166 is coupled to an input 168 of comparator 170 and through resistor 172 to an input 174 of inverter 176.

Inverter 176 acts only to invert the received signal and develop an inverted signal at output 178. The signal developed at output 178 is coupled to an input 180 of a second comparator 182. The second inputs 184 and 186 of comparators 170 and 182 respectively are coupled to the junction 188 of biasing resistors 190 and 192. Biasing resistors 190 and 192 provide a reference voltage to comparators 170 and 182 which must be exceeded in order to activate the comparators. Comparators 170 and 182 are complimentary circuits in order to provide an output indication for the condition when the output at terminal 166 of the amplifier 162 is positive or negative.

In the event that the voltages coupled to junction 150 of the summing circuit are equal, thus indicating that the rate of change voltages at times $T_1$ and $T_2$ are the same and that the reaction is proceeding linearly, then the output voltage at junction 150 will be zero. The output of amplifier 156 is some finite voltage because of the characteristics of the amplifier but is quite close to zero. Consequently, the bias voltage of amplifier 170 will not be exceeded and it will not be rendered conductive. Amplifier 176 simply inverts the sign of the signal developed at output terminal 168 so that the output of terminal 178 will be the same as the output of 166 but inverted in sign. Consequently, the voltage at input terminal 180 will not exceed the reference voltage of comparator 182 and comparator 182 will remain nonconductive.

Should the reaction become nonlinear, the voltage developed at junction 150 will no longer be zero resulting in a different voltage being developed at output terminal 166 of amplifier 162. If the different voltage is positive and exceeds the bias provided at junction 188 of resistors of 190 and 192, comparator 170 will be rendered conductive coupling a voltage from terminal 200 to terminal 202 and to lamp 50 causing illumination of the lamp. If the difference voltage developed at output 166 is negative and exceeds the bias voltage at junction 188, comparator 182 will operate coupling a voltage from terminal 204 to terminal 206 and to lamp 50 causing illumination of the lamp.

The overrange circuit previously discussed includes a comparator 210 shown in FIG. 2 having an input 212 coupled to log converter 34, a second input 214 coupled to junction 216 of resistors 218 and 220, and an output terminal 222 coupled to lamp 50. Resistors 218 and 220 are selected such that the voltage at juction 216 is 10 volts. When the voltage developed at the output of scaling amplifier 26 exceed this 10 volt reference amplifier 210 will be rendered conductive coupling the voltage at terminal 224 of amplifier 210 to terminal 222 and to lamp 50, thereby causing illumination of the lamp.

Although a particular embodiment of this system for detecting the reaction rate of change of a solution has been shown and described, it is to be understood that other modifications of the above described system are capable of being made without departing from the spirit or scope of the invention as defined in the appended claims.

What is desired to be secured by Letters Patent of the U.S. is:

1. In a reaction detection system for determining the reaction rate of a sample wherein said reaction is represented by an electrical input signal which can vary in accordance with said reaction during a predetermined time increment, the combination including;
    input means for receiving said electrical input signal,
    first sampling means coupled to said input means and operative at predetermined first intervals to sample said electrical input signal and develop a first sampling signal during said sampling proportional to said electrical input signal and to hold said first sampling signal until the following sampling,
    second sampling means coupled to said first sampling means and operative at predetermined second intervals to sample said first sampling signal and develop a second sampling signal during said sampling proportional to said first sampling signal and to hold said sampling signal until the following sampling,
    summing circuit means coupled to said first and second sampling means and operative to develop an output signal representing the difference between said first and second sampling signals, and
    display means coupled to said summing means and operative in response to said output signal to display an output proportional to said output signal.

2. The reaction detection system of claim 1 wherein said first sampling means include,
    a sample and hold circuit for sampling said electrical input signal, developing said first sampling signal and storing the same, and
    gating means coupled to said input means and said sample and hold circuit and operative at said predetermined first intervals to couple said input means to said sample and hold circuit.

3. The reaction detection system of claim 2 further including, clock means for developing first clock pulses at predetermined intervals, said gating means being coupled to said clock means and operative in response to said clock pulses to couple said input means to said sample and hold circuit.

4. The reaction detection system of claim 2 wherein said sample and hold circuit includes capacitor means coupled to said gate means for developing a voltage thereacross proportional to said electrical input signal and amplfier means coupled to said capacitor means for amplifying said voltage.

5. The reaction detection system of claim 1 wherein said second sampling means include,
    a sample and hold circuit for sampling said first sampling signal, developing said second sampling signal and storing same, and
    gating means coupled to said first sampling means and said sample and hold circuit and operative at said predetermined second intervals to couple said first sampling means to said sample and hold circuit.

6. The reaction detection system of claim 5 further including, clock means for developing second clock pulses at predetermined intervals, said gating means being coupled to said clock means and operative in response to said clock pulses to couple said first sampling means to said sample and hold circuit.

7. The reaction detection system of claim 5 wherein said sample and hold circuit includes capacitor means coupled to said gating means for developing a voltage thereacross proportional to said first sampling signal and amplifier means coupled to said capacitor means for amplifying said voltage.

8. The reaction detection system of claim 1 wherein said summing circuit means include, first resistor means having a first terminal coupled to said first sampling means and the second terminal, and second resistor means having a first terminal coupled to said second sampling means and a second terminal coupled to said first resistor means second terminal, said output signal being developed at said first and second resistor means second terminals.

9. The reaction detection system of claim 1 further including,
    third sampling means coupled to said summing means and operative at predetermined third intervals to sample said output signal and develop a third sampling signal during said sampling proportional to the output signal and to hold said third sampling signal until the following sampling,
    comparing means coupled to said summing means and operative to compare said third sampling signal and said output signal and develop a comparison signal in accordance with variations between said output and said third sampling signal, and
    indicator means coupled to said comparing means and operative in response to said comparison signal to indicate a variation between said output signal and said third sampling signal whereby an indication of the variation from linear reaction rate of change is provided.

10. The reaction detection system of claim 9 further including clock means coupled to said first, second and third sampling means and operative to develop first, second and third clock pulses at predetermined intervals, each having a predetermined repetition rate and period, said first, second and third sampling means operative in response to said first, second and third clock pulses respectively to sample and develop said sampling signals.

11. The reaction detection system of claim 10 wherein said predetermined intervals are equal.

12. The reaction detection system of claim 9 wherein said third sampling means include,
a sample and hold circuit for sampling said signal, developing said third sampling signal and storing same, and
gating means coupled to said summing means and said sample and hold circuit and operative at said predetermined third intervals to couple said summing means to said sample and hold circuit.

13. The reaction detection system of claim 12 further including, clock means for developing third clock pulses at predetermined intervals, said gating means being coupled to said clock means and operative in response to said clock pulses to couple said summing means to said sample and hold circuit.

14. The reaction detection system of claim 12 wherein said sample and hold circuit includes capacitor means for developing a voltage thereacross proportional to said summing signal and amplifier means coupled to said capacitor means for amplifying said voltage.

15. The reaction detection system of claim 9 wherein said comparing means include first resistor means having a first terminal coupled to said summing means and a second terminal and second resistance means having a first terminal coupled to said third sampling means and a second terminal coupled to said first resistance means second terminal.

16. A system for detecting the reaction rate of change of a solution whose optical opacity changes in accordance with the reaction change therein including in combination,
means for developing an electrical signal which varies in accordance with said reaction changes,
first sampling means coupled to said means for developing an electrical signal and operative at predetermined first intervals to sample said electrical signal and develop a first sampling signal during said sampling proportional to said electrical signal and to hold said first sampling signal therein until the following sampling,
second sampling means coupled to said first sampling means and operative at predetermined second intervals to sample said first sampling signal and develop a second sampling signal during said sampling proportional to the first sampling signal and to hold said second sampling signal until the following sampling,
summing circuit means coupled to said first and second sampling means and operative to develop an output signal representing the difference between said first and second signals, and
display means coupled to said summing means and operative in response to said output signal to develop an output display proportional to said output signal.

17. The system of claim 16 wherein said means for developing an electrical signal include,
a light source,
means for passing light from said light source through said solution, the light intensity passing through said solution varying in accordance with said reaction change, and
detector means for receiving said passed light and developing said electrical signal, said electrical signal varying in accordance with the intensity of said passed light.

18. The system of claim 17 wherein said means for passing light include, means for containing said solution, said means having at least two transparent portions for transmitting said light therethrough and through said solution.

19. The system of claim 18 wherein said means for developing an electrical signal further include,
chopper means for chopping said light at a regular repetition rate,
filter means for passing particular light wavelengths, the intensity of said particular wavelengths of passed light varying in accordance with the reaction rate of change of said solution,
said detector means including photodetector means positioned to receive said paritcular wavelengths of light and operative to develop an electrical photodetector signal which varies in accordance with said passed light intensity and said chopper repetition rate.
filter means coupled to said photodetector means and operative to filter said photodetector signal, to develop a detection signal, and
converter means for converting said detection signal to said electrical signal.

20. The system of claim 17 wherein said solution reaction rate of change is logarithmic, said means for developing an electrical signal including logarithmic amplifier means operative to convert said logarithmic change and develop said electrical signal having a linear reaction rate of change.

21. The system of claim 20 wherein said means for developing an electrical signal further include means for detecting said reaction change and developing a signal that varies in accordance with said reaction change, first signal adjusting means coupling said detecting means to said logarithmic amplifier means and adjustable for selecting a predetermined detection signal amplitude prior to each solution reaction, said system further including, first switching means coupling said logarithmic amplifier means to said first sampling means for selectively connecting said amplifier to said first sampling means, reference generator means coupled to said switching means and selectively operable to develop a reference electrical signal having a predetermined time rate of change and couple same to said first sampling means for establishing a reference rate of change for said system, and second switching means coupling said summing circuit means, said logarithmic amplifier means, and said first signal adjusting means to said display means for selectively displaying, said output proportional to said output signal, said electrical signal from said logrithmic amplifier and said adjusted detection signal from said first signal adjusting means.

22. The system of claim 16 further including, third sampling means coupled to said summing means and operative at predetermined third intervals to sample said output signal and develop a third sampling signal during said sampling proportional to the output signal and to hold said third sampling signal until the following sampling, comparing means coupled to said summing means and operative to compare said third sampling signal and said output signal and develop a comparison signal in accordance with the variations between said output signal and said third sampling signal, and indicator means coupled to said comparing means and operative in response to said comparison signal to indicate a variation between said output signal and said third sampling signal whereby an indication of variations in linear operation is provided.

23. The system of claim 22 further including clock means coupled to said first, second and third sampling means and operative to develop first, second and third clock pulses at predetermined intervals each having a predetermined repetition rate and period, said first, second and third sampling means operative in response to said first, second and third clock pulses respectively to sample and develop said sampling signals.

24. The system of claim 23 wherein said predetermined time intervals are equal and wherein each said first clock pulse succeeds each said second clock pulse in time and each said second clock pulse succeeds each said third clock pulse in time.

* * * * *